United States Patent [19]

Schmidt et al.

[11] 4,144,742
[45] Mar. 20, 1979

[54] MACHINE FOR TESTING BOTTLES

[75] Inventors: Dieter K. Schmidt; Josef J. Buschor, both of Los Gatos, Calif.

[73] Assignee: New Century Beverage Company, San Francisco, Calif.

[21] Appl. No.: 854,240

[22] Filed: Nov. 23, 1977

[51] Int. Cl.$^2$ .................................. G01M 3/02
[52] U.S. Cl. ................................. 73/37; 73/45.1; 141/105; 141/372
[58] Field of Search ............... 73/37, 40, 45.1, 49.2, 73/49.3, 49.4, 49.6; 141/104, 105, 107, 372

[56] References Cited

U.S. PATENT DOCUMENTS

| 280,234 | 6/1883 | Pearson | 141/105 X |
|---|---|---|---|
| 582,285 | 5/1897 | Henes et al. | 141/372 X |
| 991,664 | 5/1911 | Strasburger | 141/372 X |
| 1,022,968 | 4/1912 | Neumayer | 141/104 X |
| 2,372,899 | 4/1945 | Kantor | 141/105 |
| 2,689,475 | 9/1954 | Blanton | 73/37 |
| 3,010,310 | 11/1961 | Rowe | 73/45.1 X |
| 3,650,146 | 3/1972 | Babunovic | 73/37 |
| 3,785,195 | 1/1974 | Yasuhiro et al. | 73/37 |
| 3,805,594 | 4/1974 | Hayashi | 73/37 UX |
| 3,826,126 | 7/1974 | Yasuhiro | 73/37 |

Primary Examiner—John Petrakes
Attorney, Agent, or Firm—Edward B. Gregg

[57] ABSTRACT

Apparatus for testing bottles to determine whether they will withstand internal pressure as from a carbonated beverage, also for detecting flaws in crown of bottle which may result in leaks. Hydraulic pressure is applied internally by hydraulic fluid, usually water. Bottle is filled with low pressure water, then high pressure water is used to apply pressure. Bottle is held between a sealing chuck which contacts and seals crown and a bottom member bearing against bottom of bottle, thus simulating force applied to bottle during filling with beverage and capping. Means are provided to remove air displaced during filling with low pressure water.

13 Claims, 7 Drawing Figures

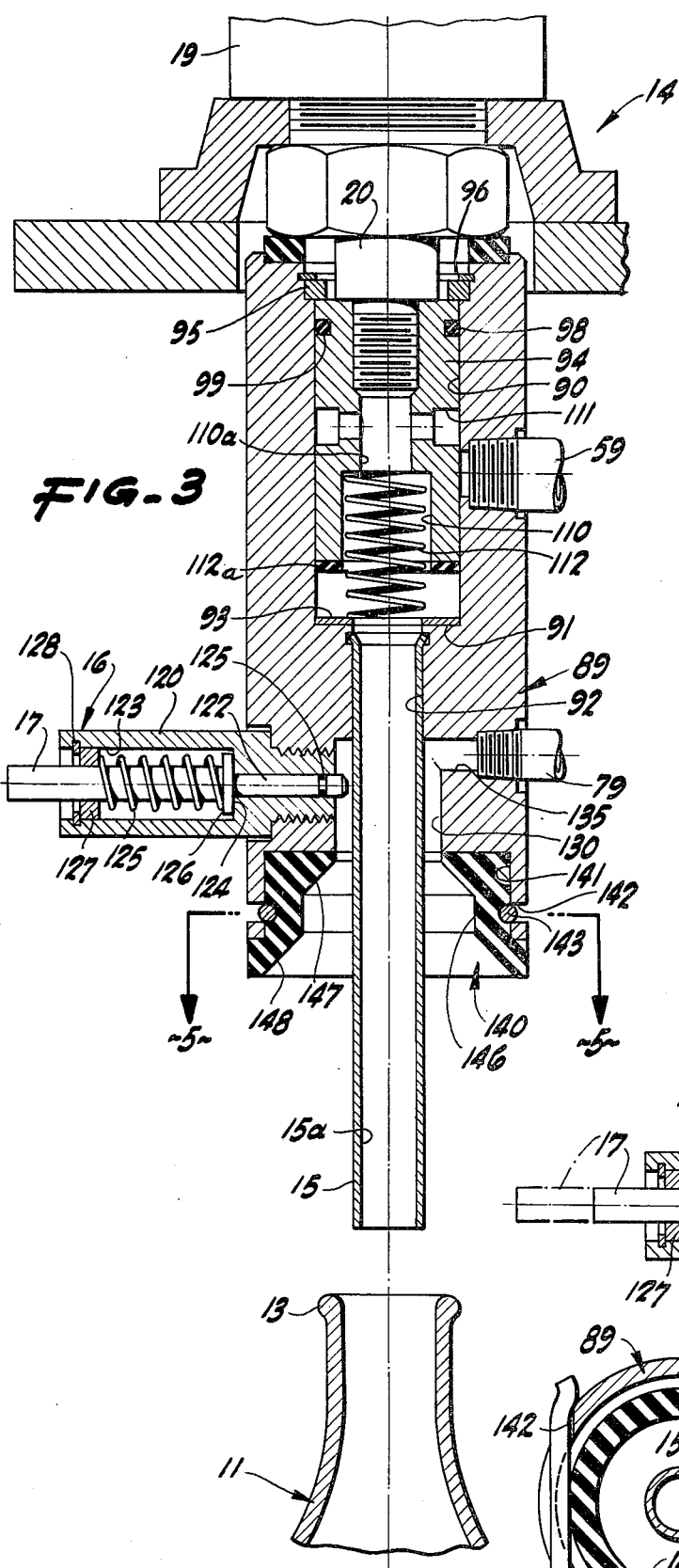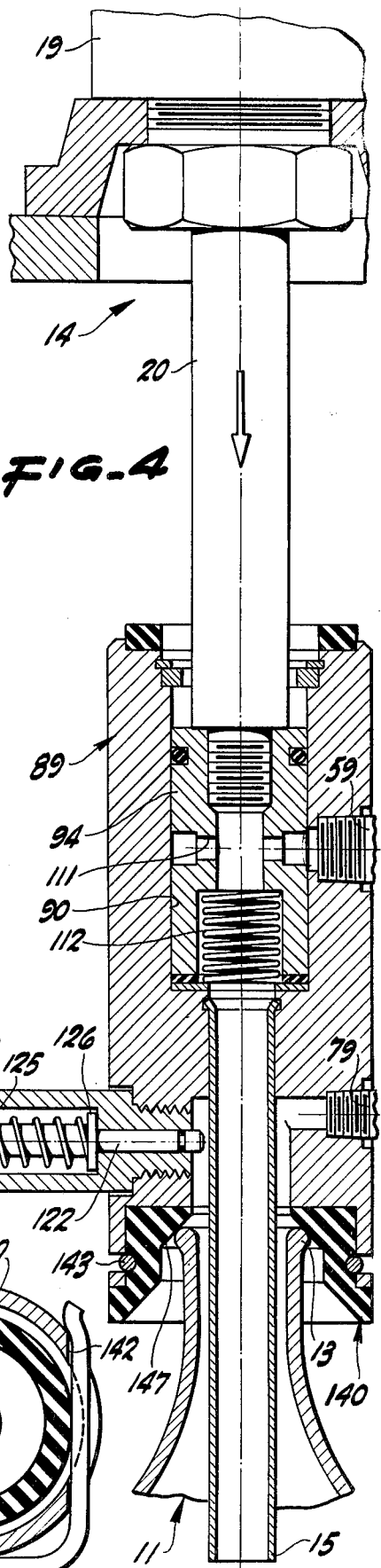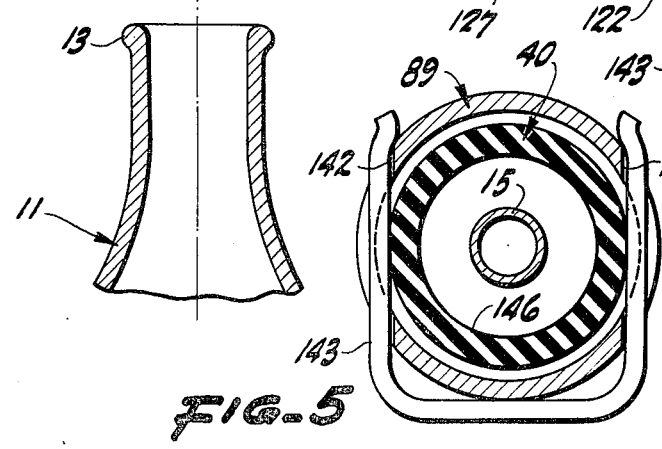

MACHINE FOR TESTING BOTTLES

This invention relates to apparatus for testing beverage bottles to determine whether they will withstand internal pressure with an adequate degree of safety.

Several different approaches have been provided or suggested to the problem of testing beverage bottles, for example, soft drink beverage bottles, both those which are carbonated and therefore generate a considerable internal pressure and those which are uncarbonated. The purpose of such testing is to determine whether the bottles are adequately strong to resist internal pressure.

One approach is to apply mechanical pressure to the exterior of the bottle. However, it is not possible to apply a uniform pressure to the entire exterior of a bottle, and it does not simulate the internal pressure applied to a bottle which has been filled with product and capped. Furthermore, this approach is not well adapted to reveal the presence of defects in the crown of the bottle which may cause leaks.

Another approach has been to apply pneumatic pressure to the interior of a bottle, but such approach is disadvantageous because when bottles fail they do so with explosive effect. The resulting shattering is hazardous to personnel and is likely to inject pieces of glass into machinery.

It is believed that the best approach to testing bottles is to fill them with the test liquid, for example water, and to apply hydraulic pressure to the filled container. This has the advantage that, if a bottle fails it does not shatter and scatter pieces of glass. With internal hydraulic pressure testing, when a bottle fails it does not do so with explosive effect. Also, it simulates the pressure to which a bottle is subjected when it is filled with product and capped.

In internal hydraulic testing one approach has been to fill bottles in a compartment where a liquid, ususally water, is showered over a large area and fills the bottles. This, however, requires the handling of a considerable quantity of water and for that reason is disadvantageous.

U.S. Pat. No. 3,826,126 describes an operation which is advantageous, namely filling each bottle in turn with low pressure water and then, when the bottle is full, introducing into the bottle water at a high pressure for the purpose of testing. However, the procedure of that patent is disadvantageous because it suspends a bottle during testing, therefore does not simulate the forces applied to a bottle during filling with product and capping; also the apparatus does not provide as good a seal while filling and testing as is desirable. Further, it is necessary during filling with low pressure water to leave clearance between the sealing chuck and the crown of the bottle for air to escape.

It is an object of the present invention to provide bottle testing apparatus employing the concept of internal hydraulic testing and employing also a cycle in which the bottle is filled first with low pressure water and is then subjected to hydraulic pressure from a high pressure water supply, but in which speed of operation is enhanced. (It will be understood that other liquids may be used in place of water, which, however, is adequate for the purpose, inexpensive and non-polluting.)

It is another object to provide a testing procedure which simulates filling of the bottle with product and capping.

It is a further object of the invention to provide hydraulic testing apparatus which maintains a seal on the bottle during low pressure filling as well as high pressure testing.

Yet another object is to provide apparatus, which will detect leaks due to faulty crowns.

The above and other objects of the invention will be apparent from the ensuing description and the appended claims.

One embodiment of the invention is shown in the accompanying drawings in which:

FIG. 3 is a vertical mid-section through the testing head shown in FIG. 2, the air cylinder operating mechanism of FIG. 2 being shown only fragmentarily, the filling spout or quill being shown in the up position before it is inserted into a bottle;

FIG. 4 is a view similar to that of FIG. 3 but showing the quill in its down position within a filled bottle, showing the sealing chuck in engagement with the crown of the bottle and showing the positions of pertinent parts while hydraulic pressure is applied;

FIG. 5 is a section taken along the line 5—5 of FIG. 3 showing the manner in which the sealing chuck is mounted;

Figure 1:
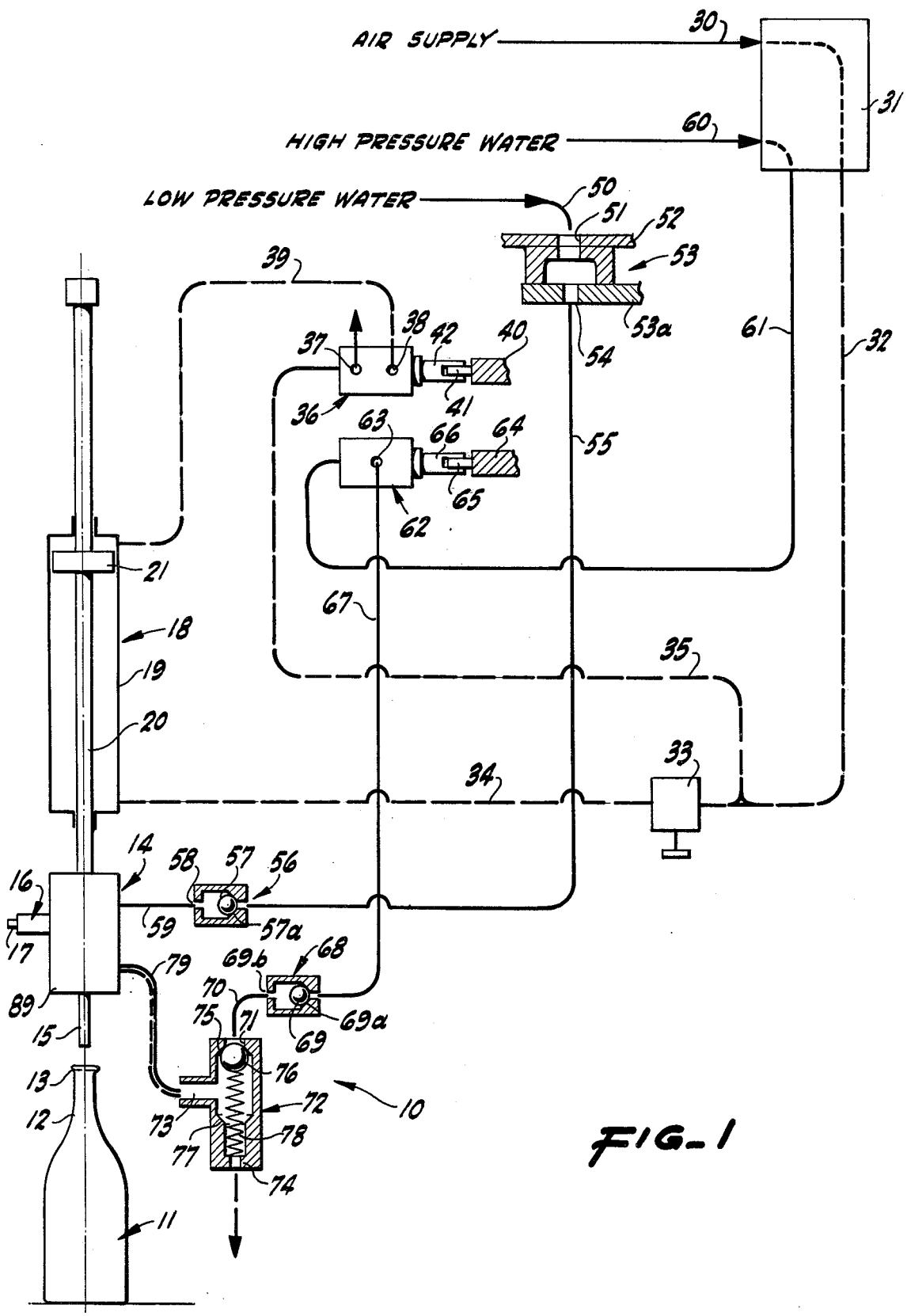
FIG. 1 is a diagrammatic view of the apparatus including its pneumatic and hydraulic circuits.

Referring now to FIG. 1, this is a diagrammatic view showing the hydraulic and pneumatic circuits and showing the apparatus of a single testing head or station. It will be understood, and it will be more fully apparent from the description hereinbelow with reference to FIG. 2 that the present invention contemplates providing a rotary turret with pockets to receive bottles in succession from a bottle entry conveyor and to rotate them through a testing station into an exit bottle conveyor to the next unit, for example, a washer to wash the bottles before they are transported to a filling machine and thence to a capping machine. Such inlet and outlet conveyors (not shown) may be of conventional type, e.g. screw conveyors. However, the invention may be employed with suitable modification for an in-line system in which there is a single testing head in line with the progression of bottles from an input point to an output point. However, it is preferred to use a rotary turret as described and illustrated hereinbelow.

Sufficient time is preferably allowed between the testing step and the washing step so that the water used for testing and still in the bottle will soak the interior of the bottle and facilitate washing. This is of importance in the processing of used returnable bottles.

The apparatus is generally designated by the reference numeral 10. A bottle 11 is shown having the usual tapered neck 12 and rolled rim or crown 13. A filling and pressure testing head or unit 14 is shown having a tube or quill 15 which is to be inserted into the bottle for the purpose of filling with low pressure water. A sensing unit 16 having a rod 17 is provided, the function and purpose of which are to sense whether a bottle has failed or has a leak and, if so, to energize a device (which is well known in the art and requires no description herein) which removes the bottle that has failed or has evidenced a leak.

A pneumatic operating and control unit 18 is provided including a cylinder 19, a rod 20 and a piston 21 which is reciprocable within the cylinder 19. Air supply line 30 (see the upper right portion of FIG. 1) connects a source of air under pressure (not shown) e.g. 80 p.s.i. gauge to a rotary valve 31 which opens and closes connection between the inlet line 30 and outlet line 32 in timed relation to rotation of the turret 140 (see FIG. 2) to provide air under pressure when and as needed and to shut off communication of air pressure when desired. Line 32 connects to a pressure reducing valve 33 of known construction and air at reduced pressure (e.g. 20 p.s.i. guage) passes through a line 34 to the lower end of cylinder 19 such that it acts to lift the piston 21.

A branch 35 in line 32 upstream from the pressure reducing valve 33 connects to a three-way valve 36 having an exhaust port 37 and a port 38 which connects to a line 39 to the upper end of cylinder 19 above the piston 21. It will be seen that relatively low pressure air is delivered to the bottom of cylinder 19 beneath the piston 21 and that relatively high pressure air is delivered to the top of cylinder 19 above the piston 21, such being carried out in the proper sequence as described hereinbelow. Valve operating means is provided in the form of a stationary cam 40 fixed to the frame of the machine which in contacted by a cam follower roller 41 which is rotatably mounted on a rod 42, the movement and position of which determine whether high pressure air is delivered through line 35, valve 36 and line 39 to the upper end of cylinder 19.

The low pressure water circuit will now be described. A line 50 connected to a source of low pressure water, for example, water at 45 p.s.i.g., connects through the inlet 51 of the stationary portion 52 of a rotary valve 53, the rotary portion being indicated by the reference numeral 53a. The rotary member 53a is formed at intervals with outlet ports 54 which connect through a line 55 to a check valve 56 having a ball 57 which seats against a seat 57a. The outlet 58 of the check valve 56 connects by a line 59 to filling and testing unit 14.

The high pressure water circuit will now be described. It comprises a line 60 connected to a high pressure source of water, for example, 150 p.s.i.g. and is in turn connected by the rotary valve 31 to a line 61. Line 61 is connected to a valve 62 having an outlet port 63 which is opened and closed by cam means including a stationary cam 64 fixed to the frame of the machine, a cam follower roller 65 and a rod 66. At the appropriate time the valve 62 is operated to connect the high pressure water supply line 61 with the port 63 whereby high pressure water is delivered through line 67 to a check valve 68 having a ball 69 seating against the seat 69a and having outlet port 69b. Line 70 connects the outlet of check valve 68 with the inlet port 71 of an air bleed or shuttle valve 72. The valve 72 has, besides the inlet port 71, outlet ports 73 and 74, a valve seat 75 for a ball 76, another seat 77 for the ball 76 and a spring 78 which normally acts to cause the ball 76 to assume the position shown in FIG. 1, i.e. closing port 71 and opening port 74. The port 73 is connected by a line 79 to the filling and testing unit 14.

Figure 2:
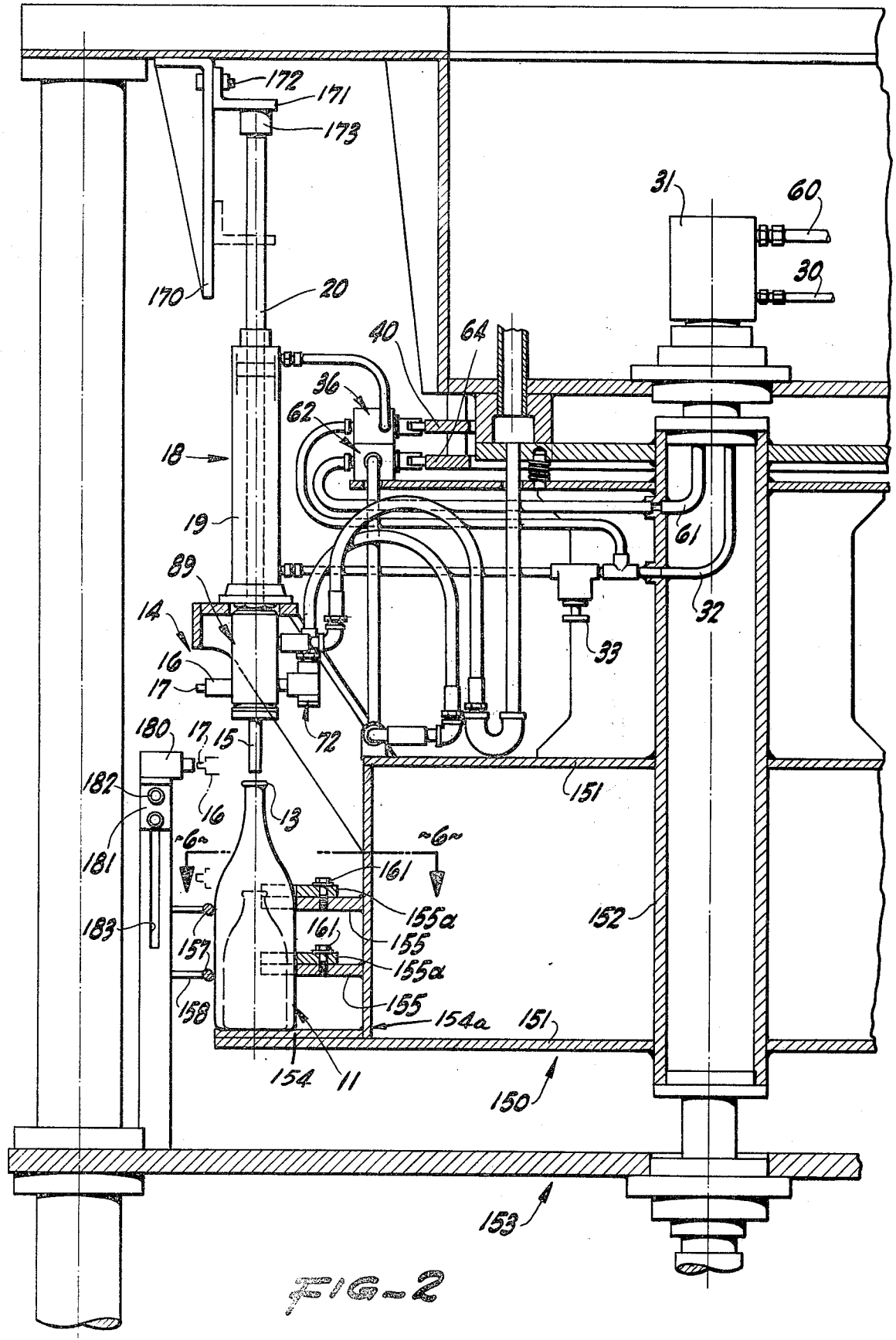
FIG. 2 is a view on a larger scale than that of FIG. 1, being a vertical mid-section through a turret showing a single filling and testing head and hydraulic and pneumatic connections to sources of air under pressure, water under low pressure and water at high pressure and showing also bottles of two different sizes and adjustments means to accommodate the different sizes.

Referring now to FIG. 2, wherein identical reference numerals identify the same parts as in FIG. 1, as will be seen many of the connecting lines are of flexible material to accommodate themselves to up and down movement of the testing head 14 and the pneumatic unit 18.

Referring now to FIG. 3, the interior construction of the filling and testing head 14 is there shown in detail. As will be seen, the head 14 comprises, as its main structural element, a cylinder 89 formed with a central cylindrical cavity 90 formed with a bottom shoulder 91 and an extension 92 of smaller diameter than the cavity 90. A washer 93 is seated on the shoulder 91. Within the cavity 90 there is a piston 94 which reciprocates within the cavity 90, its upward movement being limited by a ring 95 held in place by lock ring 96. The lower end of piston rod 20 is threaded into the piston 94. An O-ring 98 seated in an annular groove 99 in the piston 94 serves to seal the piston against the walls of the cavity 90. At its lower end the piston 94 is formed with a cavity 110 to receive a spring 112 which is confined between the washer 93 and the upper end of the cavity 110. The cavity 110 has an extension 110a of a smaller diameter which has a radial opening 111 which is intended to communicate at the proper moment with low pressure water line 59. A pad 112a secured to the lower end of piston 94 serves as a seal.

The sensor 16 comprises a body portion 120 threaded into the body 89 and formed with a passageway 122 which enlarges into a chamber 123 thus providing a shoulder 124. An O-ring 125 is provided as a seal to prevent outflow of fluid. A spring 125 confined between a collar 126 on the rod 17 and a washer 127 held in place by a lock ring 128 normally urges the rod 17 and its inner extension to the right as viewed in FIG. 3 so that the tip of the extension normally projects into an annular cavity or passage 130 surrounding the quill 15. The quill 15, as will be seen, is formed with a passage 15a.

The high pressure water line 79 is threaded into the body 89 and communicates with a radial passage 135 which in turn communicates with the annular passage 130.

A sealing chuck 140 is shown which is of rubber or resilient plastic construction and is sufficiently resilient so that under pressure it will seal firmly against the crown 13 of a bottle as shown in FIG. 4. The chuck 140 fits into a socket 141 at the lower end of the body 89. The wall of socket 141 is formed with slot 142 to receive a clip 143 which serves to hold the chuck in place but which (see FIG. 5) can be pulled out and detached for replacement of the chuck. The chuck 140 has a stepped interior configuration including a cylindrical mid-portion 146, a tapered, frusto-conical top portion 147 which seats firmly against the crown of a bottle as shown in FIG. 4 and a flaring bottom portion 148. The frusto-conical portion 147 is tangent to the outer part of the crown 13 of the bottle 11 such that it adjusts to small, normal variations in the shape of the crown. By this means the seal between the chuck 140 and the crown 13 simulates the seal between the cap and crown of the bottle when filled with product.

Figure 6:
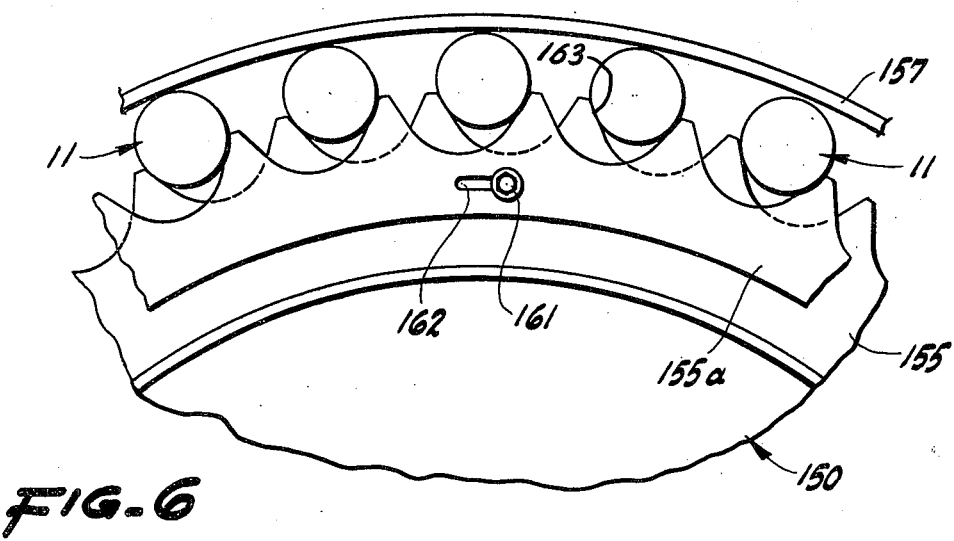
FIG. 6 is a fragmentary top plan view of the turret plates showing the manner in which the pockets in the turret are adjusted for bottles of different diameters (in this instance a small diameter)
Figure 7:
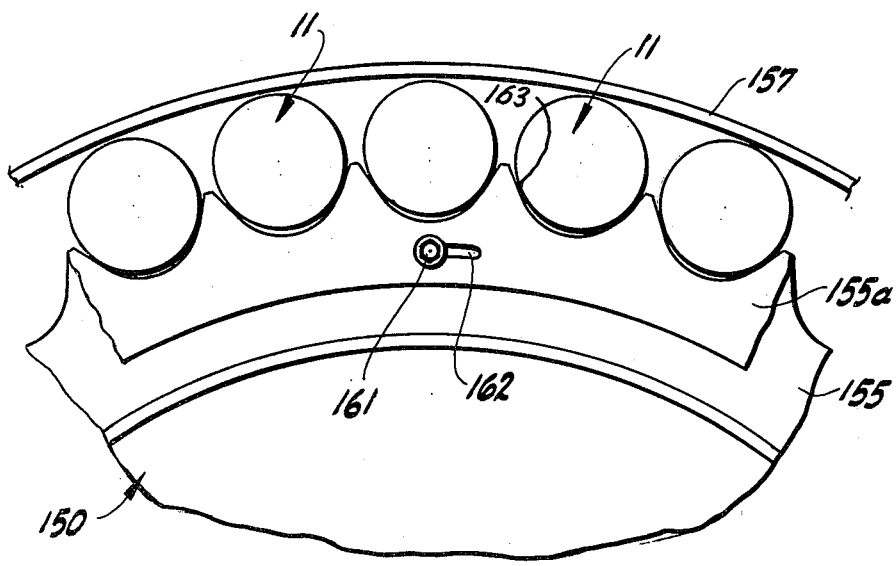
FIG. 7 is a view similar to that of FIG. 6 but showing the turret plates in adjusted position for bottles of larger diameter.

Referring again to FIG. 2, the turret which carries the several units 14 and 18 is generally designated by the reference numeral 150 and it comprises plates 151 welded to the main turret shaft 152 which is journalled in the frame 153 of the machine. To support each bottle in one of the testing units a plate 154 is provided which is part of an angle piece 154a welded or otherwise suitably connected to the frame members of the turret and upon which a bottle 11 is seated to be held in proper alignment with the quill 15. Plates of double thickness 155 and 155a are provided which cup the bottle on the inward side. Rails 157 held by brackets 158 confine the bottle on the outer side. The plates 155 and 155a are secured together by means of screws 161 and slots 162. As will be seen by reference to FIGS. 6 and 7, by loosening the screws 161 and rotating the upper plates, the pockets 163 which receive the bottles may be adjusted in size to accommodate bottles of smaller diameter (FIG. 6) or larger diameter (FIG. 7). When adjustment has been made, the screws 161 are tightened.

Also shown in FIG. 2 is height adjustment means comprising a bracket 170 secured to the frame of the machine on which an angle bracket 171 is mounted by a screw 172 in an elongated vertical slot (not shown). By loosening the screw 172, the bracket 171 may be moved up or down, for example, between the position shown in FIG. 2 for tall bottles and a lower position (not shown) for short bottles. The cap 173 on the rod 20 contacts the bracket in its up position (which is determined by the height of the bracket 171) thereby limiting upward travel of the rod 20. By this means, the travel is adjusted for a large bottle or a small bottle.

The rod 17 of sensor 16 is intended, when a bottle holds pressure properly, to contact a micro switch 180 which requires height adjustment for bottles of different heights. This is accomplished by mounting the micro switch 180 on a bracket 181 which is connected by a screw 182 to a slot 183 on a post 184, which permits height adjustment.

In operation, the apparatus functions as follows:

An infeed such as a well known type of screw feed (not shown) feeds the bottles in timed relation to rotation of the main turret shaft 152, such that each bottle in turn is deposited in a pocket 163 in the turret. Referring to FIG. 1, as each bottle in a pocket reaches a certain point, cam 40 acts on roller 41 to connect high pressure air line 35 to line 39 and thereby to cause piston 21 to undergo a down stroke together with the body 89 of head 14 and the quill 15. Referring to FIG. 4, as the chuck 140 seats on the crown 13 of a bottle as shown in FIG. 4, further downward movement of body 89 is arrested. Continued downward movement of the rod 20 acts to move piston 94 downwardly in cavity 90 against the force of spring 112, which is compressed as shown in FIG. 4. At an appropriate time rotary valve 53 (see FIG. 1) connects low pressure water line 50 with line 55 and through check valve 56 to line 59 and passage 111 in piston 94, which at this time is in alignment with line 59. Low pressure water therefore passes through passages 110a and 110 into the quill 15 and thence into the bottle. As the bottle fills, air that is displaced by the water vents through the annular space between quill 15 and the neck of the bottle, passage 135, line 79 and port 74 in shuttle valve 72. This makes it possible to fill the bottle quickly with water and the seal between the chuck 140 and the bottle is maintained during filling.

The timing is such that when the bottle is filled, cam 64 (see FIG. 1) acts on roller 65 to cause valve 62 to connect high pressure water from line 61 to line 67 and thence through check valve 68 and line 70 to shuttle valve 72. The high pressure water causes ball 76 to unseat from the position shown in FIG. 1 and to seat on the bottom seat 77, thereby closing port 74. High pressure water passes by way of line 79 to passage 135 (see FIG. 4) and through annular space 130 and chuck 140.

This high pressure acts on the inner end of rod 17 and pushes it to the outer position shown in broken lines in FIG. 4. The rod therefore contacts micro-switch 180 (see FIG. 2) which energizes (or de-energizes) a circuit to signal that pressure has been held and that the bottle is sound. If a bottle fails, or if it has a flaw which causes leakage of water out of annular space 130, the resulting signal [i.e., retention of rod 17 in its inner (full line) position] indicates a faulty bottle. A pusher or other mechanism of known construction is then activated to eject the faulty bottle. Suitable mechanisms and circuits for these functions are well known and require no description herein.

After a suitable dwell of the piston 94 in the position shown in FIG. 4, the cams 40 and 64 act to shut off the supply of high pressure water to the head 14 and of high pressure air to the top of cylinder 19, whereupon lower pressure air (which is always supplied to the bottom of cylinder 19 through line 34) acts to raise piston 21 and with it head 14 and to return piston 94 to the position shown in FIG. 3 in readiness for another cycle.

Timing is accomplished by valves 31 and 53 and by cams 40 and 64. Valve 53 is adjusted so that each bottle is slightly overfilled with water. Cam 64 is designed and/or adjusted so that high pressure water is supplied for a suitable period of time, e.g. 0.2 second in the case of conventional 6 to 8 fluid ounce bottles and to hold the high pressure for about 0.5 second. These dwell periods are, of course, subject to change according to requirements.

The tube or quill 15 may be dispensed with and the chuck 140 may be formed with inner and outer passages, corresponding to passages 15a and 130. However, a tube or quill which extends into a bottle and which forms with the chuck an annular passage is preferred.

It will therefore be apparent that a new, useful and advantageous apparatus has been provided for testing bottles by internal hydraulic pressure.

We claim:

1. Apparatus for testing a bottle at a test station with water under pressure to test the bottle for failure or for a leak, said apparatus comprising:
   (a) a test head at such station having a sealing portion and movable between a first position retracted from the bottle and a second position with the sealing portion in sealing contact with the crown of the bottle
   (b) means for automatically so moving said head
   (c) a tube carried by such head and protruding from the sealing portion of the head, said tube providing a first, central water passage and forming with the head a second, annular water passage located between the tube and the head,
   (d) means for automatically supplying low pressure water through the tube to the bottle when the head is in its second, sealing position sealed to a bottle at said test station,
   (e) air venting means operable to vent air displaced by low pressure water through said annular passage,
   (f) means for automatically supplying high pressure water through said annular passage to said bottle when the bottle is filled with low pressure water,
   (g) means actuated by drop of pressure when high pressure water is supplied to the bottle to sense a failure or a leak and (h) means for automatically retracting the test head at the conclusion of the pressure test.

2. A test apparatus for supplying low pressure and high pressure water to a bottle to be pressure tested at a testing station said apparatus comprising:
   (a) a test head movable between a first retracted position separated from a bottle at the test station and a second sealing position in sealing contact with such bottle, said head having a sealing portion
   (b) a tube carried by the test head and projecting from the sealing portion thereof to penetrate the bottle when the test head is in its second position, said tube providing a first, central passage for low pressure water into a bottle and forming with the head a second, annular passage between the test head and the tube for passage of high pressure water into the bottle,
   (c) said head being provided with a first duct for communicating said annular passage with a source of high pressure water
   (d) said head being also provided with a second duct for communicating said tube with a source of low pressure water
   (e) a valve member reciprocable within said head between a first position closing said second duct and a second position opening said second duct and
   (f) means normally holding said valve in its first position but acting to move the valve to its second position when the body is in sealing engagement with a bottle.

3. The test apparatus of claim 2 wherein said valve member (e) is in the form of a piston reciprocable within said head between a first position closing said second duct and a second position exposing said duct, a spring within the head acting normally to hold said piston in its first position and yielding when the head makes sealing contact with a bottle and an axial force is applied to move the piston to its second position.

4. Pressure testing apparatus for applying hydraulic pressure to the interior of a bottle comprising:
   (a) means for holding a bottle upright at a test station with its neck uppermost.
   (b) a test head mounted for vertical movement between an up position retracted and separated from the bottle and a down position in sealing contact with a bottle at said station
   (c) said head having an axial passage and a tube within such passage projecting beyond the lower end of the head such that it penetrates a bottle at the test station when the head is in its down position and in sealing engagement with the bottle, said tube and head forming an annular passage for flow of water into a bottle
   (d) means for automatically moving said head in a repetitious cycle comprising a down movement to seal against a bottle and to cause the tube to penetrate the bottle, a dwell during filling and testing and an up movement after testing has been completed to retract the head and tube from the bottle
   (e) means for automatically supplying low pressure water to said tube to fill the bottle during the first portion of the dwell part of the cycle
   (f) means for automatically supplying high pressure water to said annular passage during a subsequent portion of the dwell part of the cycle to apply a test pressure to the bottle
   (g) means for terminating flow of both low pressure and high pressure water before the end of the dwell part of the cycle and
   (h) means for automatically retracting the head and tube from the bottle at the conclusion of the dwell part of the cycle.

5. The apparatus of claim 4 including:
   (a) a low pressure water supply circuit including automatic valve means acting to connect a source of low pressure water with said tube during the first part of the dwell and including a check valve to prevent backflow of water in said circuit, and
   (b) a high pressure water circuit including automatic valve means for connecting a high pressure source of water to said annular space during a later part of the dwell.

6. Apparatus for rapidly filling a container with a low pressure liquid and then supplying a high pressure liquid to the container to pressure test the container, said apparatus comprising:
   (a) a sealing and liquid supply head movable between a retracted position separated from a bottle at a test station to allow movement of a bottle into and out of such station and a second position in sealing engagement with the container at the test station for filling and for application of hydraulic pressure
   (b) a tube carried by and projecting from the head to penetrate the container when the head is in its second, sealing position to supply a low pressure liquid to the container, said tube and head forming an annular passage between the tube and the head for passage of high pressure liquid
   (c) a low pressure circuit for supplying a low pressure liquid through the tube to the container to fill the container rapidly
   (d) means for venting displaced air during the filling step through said annular passage
   (e) a high pressure supply circuit for supplying high pressure liquid to the filled container through said annular passage to pressure test the container and
   (f) valve means in the high pressure circuit adapted to function as an air bleed for displaced air during the filling operation and to allow introduction of liquid under pressure during the high pressure testing operation.

7. Apparatus for pressure testing containers comprising:
   (a) a container support at a test station for supporting a container with its opening uppermost
   (b) a test head mounted for movement between an up position separated from a container at the test station and a down position in sealing engagement with the container, said test head including a tube for passage of low pressure water, said tube projecting from the lower end of the test head and into the container when the test head is in its down position, said head and tube providing also an annular passage for high pressure water
   (c) means for moving said head automatically through a repetitious cycle including a downward movement into sealing engagement with a container, a dwell following such downward movement during filling and pressure testing and retraction after completion of testing
   (d) low pressure supply means and high pressure supply means for, respectively, filing the container through the tube with low pressure water and then applying high pressure water to the filled container to pressure test it, said high pressure supply means acting also to vent air displaced during the filling part of the dwell (e) and means for moving the test head between its up and down positions, said means including an air cylinder, a piston reciprocable within the cylinder and a rod connecting the piston to the test head, a high pressure air supply to the cylinder above the piston to cause its downward movement and sealing engagement with the container and a low pressure air supply to the cylinder beneath the piston operable when the high pressure air supply is terminated to move the piston and with the test head upwardly to their up positions.

8. In bottle testing apparatus of the internal hydraulic pressure type wherein a bottle is first filled with water at low pressure, air displaced during filling is vented and then high pressure water is applied to the filled bottle, the improvement which comprises:

(a) a sealing head for sealing against the crown of the bottle during filling and testing, (b) a central duct projecting from the sealing head and penetrating the bottle during filling and testing, said duct and head forming a space therebetween, and (c) pressure sensing means carried by the head and exposed to pressure in said space to sense the maintenance of pressure in the bottle and to sense loss of pressure due to failure or a leak.

9. The improvement of claim 8 wherein said pressure sensing means includes a rod exposed to pressure in said space and reciprocable within a passage and means acting on the rod at low pressure to urge the rod to a first position upon failure of pressure and yielding to pressure when a bottle is sound.

10. Bottle testing apparatus of the type wherein the bottle to be tested is first filled with low pressure water and then high pressure water is applied to the filled bottle, comprising:

(a) a test head having a first passage for flow of low pressure water into the bottle while the crown of the bottle is sealed by said head, and a second passage for outflow of displaced air during filling and for input of high pressure water during testing, (b) a low pressure water supply and means connecting said first passage with said supply during a filling step, said second passage serving to vent air that is displaced during filling, (c) a high pressure water supply and means connecting said second passage to such supply when the bottle was been filled, and (d) means for establishing communication of said low pressure supply with said first passage during the filling step, and (e) means for closing communication of said low pressure supply to said first passage and for establishing communication of said high pressure water supply to said second passage during the pressure testing step.

11. In a bottle testing machine wherein a bottle is sealed by a sealing chuck, is filled with water at low pressure and is then submitted to high pressure water for testing, the improvement which comprises a sealing chuck having passages for inflow of low pressure water, outflow of displaced air and inflow of high pressure water, said chuck having a tapered inner sealing surface which is tangent to the exterior of the crown of the bottle during the filling and pressure testing steps.

12. Bottle testing apparatus comprising a filling and testing station including a bottom support for a bottle, a bottle filling and pressure applying unit which is reciprocable between an up position clearing a bottle at such station and a down position for sealing engagement with the top of a bottle at such station, said unit including a first passage for inflow of water at low pressure during filling of the bottle and a second passage for outflow of displaced air during such filling and for inflow of high pressure water for pressure testing, a source of water under low pressure, a source of water under high pressure, means including a check valve for supplying low pressure water to said first passage during filling of the bottle, said check valve acting to prevent reverse flow of water through said first passage, means connecting said high pressure source of water to said second passage including a valve serving during filling of a bottle with low pressure water to vent air displaced from the bottle during filling and acting, when high pressure water is applied to said second passage, to prevent outflow of high pressure water.

13. A method of testing bottles comprising:

(a) sealing the top of a bottle resting on a bottom support and filling the bottle with water at low pressure, meanwhile venting displaced air from the bottle without breaking the seal (b) then applying high pressure water to the water in the filled container while the bottle is clamped between the top seal and the bottom support (c) holding the filled bottle with applied pressure for a short period of time and (d) sensing loss of pressure due to failure of the bottle or leakage at the top of the bottle at the point of sealing.

* * * * *